United States Patent [19]
Waller

[11] Patent Number: 5,965,540
[45] Date of Patent: *Oct. 12, 1999

[54] **CINNAMOYL-C-GLYCOSIDE CHROMONE ISOLATED FROM *ALOE BARBADENSIS***

[75] Inventor: Todd A. Waller, Harlingen, Tex.

[73] Assignee: Univera Pharmaceuticals, Inc., Broomfield, Colo.

[ * ] Notice: This patent issued on a continued prosecution application filed under 37 CFR 1.53(d), and is subject to the twenty year patent term provisions of 35 U.S.C. 154(a)(2).

[21] Appl. No.: 08/686,270

[22] Filed: Jul. 25, 1996

Related U.S. Application Data

[63] Continuation of application No. 08/391,139, Feb. 21, 1995, abandoned.

[51] Int. Cl.$^6$ ................................................. A01N 43/04
[52] U.S. Cl. ........................... 514/25; 536/4.1; 435/195.1
[58] Field of Search ........................ 536/4.1; 435/195.1; 514/25

[56] References Cited

U.S. PATENT DOCUMENTS 4,966,892  10/1990  McAnalley ................................. 514/54

OTHER PUBLICATIONS

Pelley et al., Seifen, Oele, Fette, Wachse (1993), 119(5), 255–260.

Chemical Abstracts, vol. 112, issued 1990 (Columbus, OH. USA), 'Anthracene and chromone derivatives in the exudate of *Aloe rabaiensis*'. The abstract No. 155211, J, Conner, et al., Phytochemistry, 28(12), 3551–3 (Eng), 1990.

Speranza et al, Aloeresin C, A Bitter C, O–Diglucoside from Cape Aloe, Phytochemistry, 1985, vol. 24, No. 7, pp. 1571–1573.

Speranza et al, Aloe Revisited—The Structure of Aloeresin A, Tetrahedron Letters, 1982, vol. 23, No. 23, pp. 2423–2424.

Strickland et al, Prevention of Ultraviolet Radiation–Induced Suppression of Contact and Delayed Hypersensitivity by *Aloe barbadensis* Gel Extract, The Journal of Investigative Dermatology, Feb., 1994, vol. 102, No. 2, pp. 197–204.

Udupa et al, Anti–Inflammatory and Would Healing Properties of *Aloe vera*, Fitoterapia, vol. LXV, No. 2, 1994, pp. 141–145.

Yagi et al, Structure Determination of Polysaccharides in *Aloe arborescens* var. *natalenses*, Planta Medica, 1986, pp. 213–218.

Davis et al, *Aloe vera* as a Biologically Active Vehicle for Hydrocortisone Acetate, Journal of the American Podiatric Medical Association, Jan., 1991, vol. 81, No. 1, pp. 1–9.

Davis et al, Processed *Aloe vera* Administered Topically Inhibits Inflammation, Journal of the American Podiatric Medical Association, Aug., 1989, vol. 79, No. 8, pp. 395–397.

Henry, R., An Updated Review of *Aloe vera*, Cosmetics & Toiletries, Jun., 1979, vol. 94, pp. 42–50.

Holdsworth, D.K., Chromones in Aloe Species Part I—Aloesin—a C–glucosyl–7–hydroxychromone, PM, vol. 19, No. 4, pp. 322–325.

Holdsworth, D.K., Chromones in Aloe Species Part II—Aloesone, PM, 22(1), pp. 54–58.

Speranza et al, A C–Glucosylated 5–Methylchromone from Kenya Aloe, Phytochemistry, 1986, vol. 25, vol. 25, No. 9, pp. 2219–2222.

*Primary Examiner*—Irene Marx
*Attorney, Agent, or Firm*—Swanson & Bratschun LLC

[57] ABSTRACT

A composition of matter comprising at least 15% by weight of the compound: 8-C-β-D-[2'-o-(E)-cinnamoyl]glycopyranosyl-2-[(S)-2-hydroxyl]propyl-7-methoxy-5-methylchromone. This compound, found in very small amounts in leaves of the *Aloe Barbadensis* plant, when concentrated to the desired level, exhibits anti-inflammatory activity.

4 Claims, 1 Drawing Sheet

CINNAMOYL-C-GLYCOSIDE CHROMONE ISOLATED FROM *ALOE BARBADENSIS*

This application is a continuation of application Ser. No. 08/391,139 filed Feb. 21, 1995 now abandoned.

BACKGROUND OF THE INVENTION

The present invention describes a compound having biological activity which has been isolated from the *Aloe barbadensis* plant. This heretofore-unreported compound, systematically named 8-C-β-D-[2'-o-(E)-cinnamoyl] glycopyranosyl-2-[(S)-2-hydroxy]propyl-7-methoxy-5-methylchromone; has a molecular weight of 541 Da, and the following chemical structure:

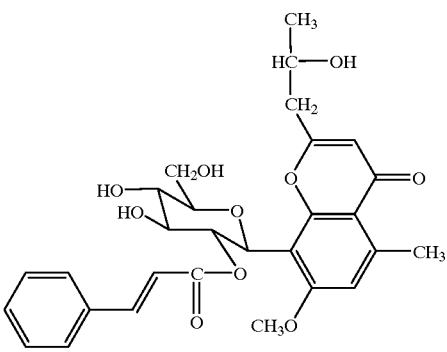

This compound exhibits potent anti-inflammatory activity as measured in vivo assays. The compound has also been shown to inhibit EGF-induced DNA synthesis in in vitro testing in epithelial cell lines.

Exudates from aloe plants have been employed for centuries as folk remedies for the treatment of burns, sores and other wounds. In recent years, a great deal of research has been concentrated on identifying aloe components which have clinical activity. Two factors which prompt this interest are aloe's propensity to lose at lease some of its therapeutic properties shortly after harvesting, and the desire to eliminate components which may be harmful—e.g., certain anthraquinones. See, e.g., McAnalley, U.S. Pat. No. 4,966, 892. The results of these research efforts suggest that the aloe plant contains several components which have wound-healing properties.

The literature contains a report of a 5-methylchromone C-glucoside which has been identified in Cape Aloe, viz., 2-acetonyl-7-o-β-D-glucopyranosyl-8-C-β-D-[2'-o-(E)-p-coumaroyl]glucopyranosyl-5-methyl-chrome. Giovanna Speranza, P. Gramatica, G. Dada, P. Manitto, "Aloeresin C, A Bitter C,o-Diglucoside from Cape Aloe", *Phytochemistry*, 1985, 24(7):1571–1573. This prior art compound has a molecular weight of 556.5 Da, the glycosylation group is coumaric acid, not cinnamic acid, and no biological activity is ascribed to the compound.

Other reports of chromones in aloe are found in the literature. "Aloe Revisited—The Structure of Aloeresin A", P. Gramatica, D. Monti, G. Speranza, P. Manitto, *Tetrahedron Letters*, 1982, 23(23):2423–2424; "Chromones in Aloe Species Part 1. Aloesin—a C-glucosyl-7-hydroxy-chromone", D. K. Holdsworth, *PM*, 19(4):322–325; "Structure Determination of Polysaccharides in *Aloe arborescens var. natalensis*", Akira Yagi, H. Nishimura, T. Shida, I. Nishioka, *Planta Medica*, 1986, 213–218; "Chromones in Aloe Species Part II—Aloesone", D. K. Holdsworth, *PM*, 22(1):54–58; and "A C-Glucosylated 5-Methylchromone from Kenya Aloe", Giovanna Speranza, G. Dada, L. Lunazzi, P. Gramatica, P. Manitto, *Phytochemistry*, 1986, 25(9):2219–2222.

SUMMARY OF THE INVENTION

The present invention relates to a composition of matter which contains 8-C-β-D-[2'-o-(E)-cinnamoyl] glycopyranosyl-2-[(S)-2-hydroxy]propyl-7-methoxy-5-methylchromone (hereafter, the "540 Compound") at a concentration of at least 15% by weight. In vivo data indicates that concentrations below about 15 % by weight do not result in statistically significant anti-inflammatory activity. The balance of the composition can contain polysaccharides normally found in Aloe (chiefly manoses), Aloin, conjugated anthaquinones, conjugated chromones and anthraquinone aglycones. The balance of the composition can also include any of the liquid carriers or vehicles commonly used to formulate ointments or lotions, such as emulsified fatty alcohols, ethoxylated stearyl alcohols, fatty ether phosphates (e.g., oleyl ether phosphates), ethoxylated lanolin alcohols, beeswax, glycerol monostearate, emulsified polydimethylsiloxanes, glycerin, mineral oil and surfactants. Other suitable vehicles will be apparent to formulators of ointments and lotions.

The previously-unidentified 540 Compound is found in the *Aloe barbadensis* plant at very small levels: in decolorized gel (the most commonly used form of aloe) at <>0.0001% by weight; in non-decolorized gel at <0.0011% by weight; in decolorized whole leaf extract at <0.0002% by weight; and, in non-decolorized whole leaf extract at <0.0025% by weight. Thus, in order to prepare compositions having the desired clinical properties, it is necessary to treat liquid solutions containing dissolved or suspended aloe extracts in order to concentrate the 540 Compound to the desired level of 15 % or more.

Prior art experiences with aloe plant extracts has shown that the majority of the biologically-active components in the plant are located in the clear gel found in the core of aloe leaves. We have found the 540 Compound in such gels; however, as noted above, we have discovered that the 540 Compound is present in greater levels in the leaf rind.

Two processes have been developed for concentrating the 540 Compound. In the first process, freshly-harvested leaves from the plant *Aloe barbadensis* were washed, gel was separated from the rind, and the gel-containing liquid slurry was filtered to remove solid particles. (Because of the greater levels of 540 Compound in the leaf rind, an alternative, preferred, procedure would be to grind the whole leaf to form a slurry).

Dialyization of the filtrate (Spectraphor #1 tubing, 24 hours×3) resulted in two fractions—the dialysate and the retained material. Two liters of 80% ethanol was added to a 500 mL portion of the retained material (~10 g solids), the sample was agitated and centrifuged at 20,000 rpm for 15 minutes, and the precipate was discarded. Ethanol was stripped from the supernatant in a rotoevaporator, yielding 1.31 grams of a product. A 1.14 gram sample of this product was extracted with a mixture of $CHCl_3$ and water which partitioned the sample into the aqueous phase and organic phase in the ratio of 3:1, respectively.

The chloroform phase was evaporated and lyophilized, and then taken up in 50% ethanol to a concentration of 20 mg/ml. This sample was analyzed using high performance liquid chromatography (HPLC). A pool eluting from an ODS 1 column at about 14 minutes was found to contain a component which inhibited DNA synthesis induced by EGF in NMuMG epithelial cells. Subsequent analysis revealed this to be the 540 Compound.

Several commercial processes employed in the processing of *Aloe barbadensis* gel utilize activated charcoal to improve the color of material. This treatment is particularly common with so-called "whole-leaf processing" wherein the entire leaf is ground and processed. Whole leaf processing produces a darker product than that which is produced using gel which has been separated from the leaf rind. However, when the dialysis separation outlined above was repeated on such charcoal-treated material, the product did not exhibit the same level of biological activity.

One hypothesis was that the factor which was responsible for the biological activity had been trapped or entrained on the activated charcoal. Subsequent testing confirmed this hypothesis. Elution of activated charcoal with organic solvents which had been used to treat a slurry of ground *Aloe barbadensis* leaves produced a solution which contained the 540 Compound. Details of this processing are set out in the following examples. Data relating to in vivo testing of the 540 Compound are set out at FIG. 1.

Example I

Figure 1:
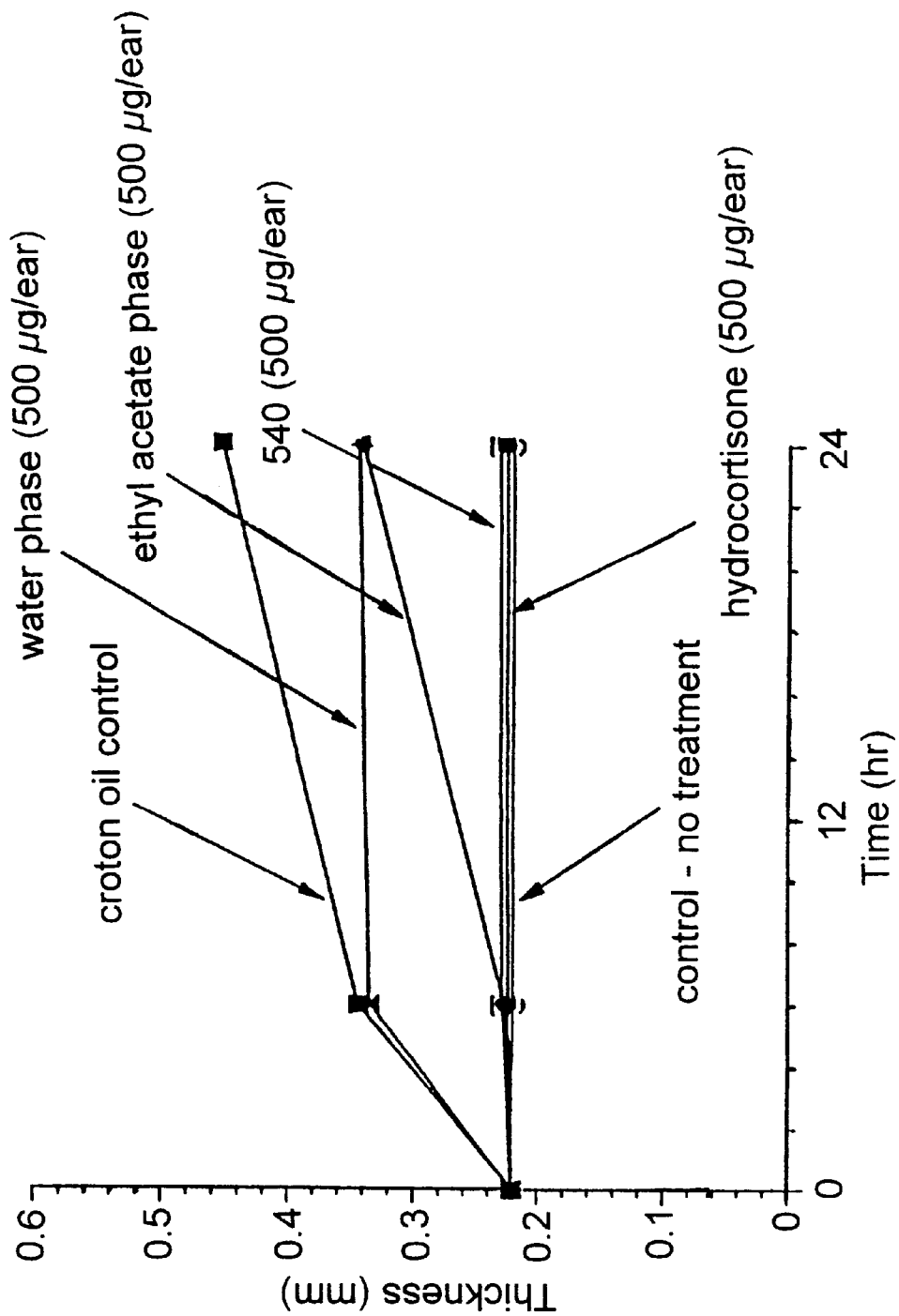
FIG. 1 illustrates the topical anti-inflammatory activity of the 540 Compound in comparison with other *Aloe barbadensis* extracts and hydrocortisone when tested on laboratory mice. Data points represent the mean ±sd for three mice. Irritant alone was utilized for the "croton oil control" group. The "control—no treatment" group data were obtained from untreated ears. Ear thickness was measured by means of an Oditest caliper.

Separation of 540 Compound from Activated Charcoal 150 g of activated charcoal which had been used in the processing of *Aloe barbadensis* whole leaf extract was subjected to two cycles of elution with refluxing 25% Acetone in $CH_2Cl_2$. The first elution was conducted with 750 mL (because of the need for "wetting" of the dried adsorbed charcoal). After extraction for four hours with stirring, the liquid was separated by filtration on a cellulose filter and the moist cake was washed with 250 mL of the eluting solvent. The moist cake was then extracted with the same solvent system (500 mL) for 7 hours. The second elute was removed as above and the moist cake washed. The Acetone/$CH_2Cl_2$ eluates were combined with their respective washes and were stripped by rotary evaporation under reduced pressure. The oily residue was transferred to scintillation and evaporation completed under a stream of nitrogen. The residues were dissolved in absolute Ethanol (EtOH) at a concentration of 100 mg/mL. The third and fourth elutions were performed with refluxing absolute EtOH. Each elution employed 500 mL. After the third elution, the wash was kept separate from the eluate and there was no wash after the fourth elution. Stripping of the third eluate, wash after third elution and the fourth eluate yielded syrups. These were dried under high vacuum for three days. The residues were dissolved in 50% EtOH in water to 100 mg/mL (wash after third elution and fourth eluate) or 200 mg/mL (third eluate). Dilutions of 10 mg/mL were made of all eluates as stocks for analysis.

Since the first and second eluates (25% Acetone/$CH_2Cl_2$) so closely resembled each other, they were pooled into Pool A. In similar fashion, the third eluate, the wash after the third eluate and fourth eluate closely resembled each other, and were pooled into Pool B. HPLC analysis was performed on A and B.

The composition of the two samples is set out in Table I:

TABLE I

COMPOSITION OF ELUATE POOLS

| | 25% Acetone $CH_2Cl_2$ Eluate A | Ethanol Eluate B |
|---|---|---|
| Mass | 1,219 mg | 6,970 mg |
| 540 Compound kUnits/mg Total | 1,998 | 925 |
| 540 Compound MUnits | 2.43 | 6.45 |
| Estimated Aloin[1] | 4.3% | 13.1% |
| Estimated Total Aloin | 53 mg | 912 mg |
| Total Hexose | 3.75 ± 0.15% | 32.2 ± 3.8% |
| Aloin Hexose[2] | 1.5% | 4.6% |
| Non-Aloin Hexose | 2.25% | 27.2% |

[1] From HPLC, integration of arbitrary ODU areas under the curve.
[2] Dubois Assay, direct determination on Pool.

Samples of the two products were lyophilized and tested for anti-inflammatory activity on laboratory mice. In addition, the samples were analyzed to confirm the chemical structure of the active component.

Example II

Confirmation of Chemical Structure

Structural elucidation of the cinnamoyl-C-glycoside chromone found in the sample, Eluate A, prepared in accordance with Example I, was accomplished by use of nuclear magnetic resonance ($^1H$) spectroscopy and mass spectrometry, evaluation of ultraviolet absorbance, melting point and thin-layer chromatographic behavior. The results were as follows:

(1) Analytical data and methodology

Melting point: sublimes >90° C.

Thin-layer chromatography

TLC plate: silica

Solvent system: ethyl acetate/methanol/water (100:13:3, v/v/v)

$R_f$: 0.69

UV spectrum

Solvent: $CH_3OH$ $\lambda_{max}$ (log ε): 246 nm (4.22), 254 nm (4.27), 284 nm (4.36)

Proton NMR analysis

Instrument: General Electric model QE 300 spectrometer

Frequency: 300 mHz

Solvent: $CD_3OD$

Reference: $CH_3OH$, 3.30 ppm

Spectral data: 1.30 (3H, d, 6 Hz) (2-γ-methyl); 2.74 (3H, s) (5-methyl);

2.82 (2H, dd, 14 Hz, 6.5 Hz) (2-α-methylene);

3.42–3.50 (1H, m) (5'-H); 3.61 (1H, dd, 10 Hz) (4'-H); 3.70–3.80 (2H, m) (3'6'a-H);

3.89 (3H, s) (7-methoxy); 4.00 (1H, m) 6'b-H);

4.37 (1h, m) (2-β-carbinol); 5.21 (1H, d 10 Hz) (1'-H);

5.73 (1H, dd, 10 Hz) (2'-H); 6.13, (1H, s) (3-H); 6.27 (2H)

(1H, d 16 Hz) (cinnamoyl β-H); 6.81 (1H, s) (6-H); 7.37 (2H, m) (cinnamoyl m-H); 7.45 (1H, d, 16 Hz) (cinnamoyl α-H);

7.50 (3H, m) (cinnamoyl o-, p-H)

Mass spectral analysis

Instrument: Finnigan MAT 4615 quadrupole mass spectrometer

Ionization: electron impact (70 eV)

Source temperature: 160° C.

Sample introduction: direct insertion probe

Sample heating: ballistic; peak evaporation at approximately 250° C.

Spectral data (relative intensity in parenthesis):

m/z 540 (12), $[M]^+$; m/z 522 (5), $[M-H_2O]^+([M-18]^+)$; m/z
496 (4), $[M-CH^3CHO]^{+(1)}$ $([M-44]^+)$; m/z 410 (16), $[M-cinnamoyl]^{+(2)}$ $([M-130]^+)$; m/z 392 (10), $[M-(130+18)]^+$; m/z
376 (4), $[M-(18+cinnamate)]^{+(2)}$ $([M-(18+146)]^+)$; m/z 366
(8), $[M-(130+44)]^+$; m/z 343 (18), $[M-18+147+33)]^+$ (3); m/z
277 (50), $[M-(130+133)]^{+(4)}$; m/z 259 (100), $[M-(130+18+133)]^+$;
m/z 233 (92), $[M-(130+44+133)]^+$; m/z
193 (73), $[M-(130+84^{(5)}+133)]^+$; m/z 131 (40), $[cinnamoyl]^+$;
m/z 103 (33), $[C_6H_5CHCH]^+$

[1] alpha-cleavage of the 2-hydroxypropyl side chain [2] involves hydrogen transfer [3] tentative assignment [4] 133 represents C2–6 of the C-glycoside [5] retro-Diels-Alder fragmentation that includes the hydroxy-propyl side chain

Example III

Biological Activity

Samples of Eluate A and Eluate B prepared in accordance with Example I were dissolved in ethanol (100 mg/mL) and tested on mice in accordance with the following procedure.

In order to induce ear swelling, a solution of croton oil was applied to the inner side of the ear of laboratory mice. The test materials were applied to the same location 30 minutes after the croton oil treatment. Measurements of ear thickness were made 18 hours after treatment. The results are shown in Table II.

TABLE II

ANTI-INFLAMMATORY ACTIVITY OF ELUATE POOLS

| | 25% Acetone CH$_2$Cl$_2$ Eluate A | Ethanol Eluate B | Standard Aloe Gel[1] |
|---|---|---|---|
| Dose Applied to Ear | 100 μg | 100 μg | 400 μg |
| Croton Oil Induced Swelling[2] | 4.1 ± 0.3 | 5.8 ± 0.4 | 5.2 ± 0.4 |
| % Inhibition of Swelling[3] | 43.4 ± 3.9% | 21.1 ± 1.3% | 29.0 ± 2.2% |

[1]*Aloe barbadensis* gel supplied by Aloecorp, Irving, Texas.
[2]Milligrams of experimental ear punch - milligrams of control ear punch. Mean ± Standard Error of the Mean, groups of 12 animals each.
[3]Untreated ear injured with 25 μg of Croton oil, swelling was 7.3 ± 0.3 mg.

Example IV

Measurement of Anti-Inflammatory Activity

A lyophilized sample of a product prepared in accordance with Eluate A of Example I was extracted into methanol, and the solvent evaporated in vacuo. The residue was dissolved in water and partitioned between water and ethyl acetate. The respective solvents were removed in vacuo and the remaining solid tested in parallel with the 540 Compound for topical anti-inflammatory activity. The results of this experiment are reproduced graphically at FIG. 1. From this experiment, it can be seen that the 540 Compound exhibits potent anti-inflammatory activity—comparable to an equal dose of hydrocortisone. Ear thickness after treatment with the 540 Compound was significantly less than the croton oil control group; statistical significance was determined by a one-way analysis of variance, with multiple comparisons assessed by Fisher's PLSD. Moreover, a 500-μg portion of the ethyl acetate phase components was similarly active at 6 hours after treatment, but showed diminished potency at 24 hours. Components in the water phase were only slightly active at 24 hours after treatment.

Male Balb/c mice weighing 20–25 g were utilized for these experiments. Three animals were used for each group. In order to induce ear swelling, 10 μL of croton oil solution (25 mg croton oil dissolved in a vehicle of pyridine/water/diethyl ether (4:1:5, v/v/v)) was applied by means of an Eppendorf pipette to the inner side of the left ear of each mouse. Each test material was dissolved in the same vehicle and applied to the same location on the left ear, 30 minutes after croton oil treatment. Animals treated with hydrocortisone were evaluated in parallel as a model for potent anti-inflammatory activity. Ear swelling in a control group in which animals were treated with croton oil alone was also assessed. Ear thickness was measured by means of an Oditest caliper. Measurement was made before application of croton oil, and at 6 and 24 hours after treatment with the test solutions.

The results of this testing are depicted in FIG. 1.

What is claimed is:

1. A composition of matter comprising at least 15% by weight of the compound: 8-C-β-D-[2'-o-(E)-cinnamoyl]glycopyranosyl-2-[(S)-2-hydroxy]propyl-7-methoxy-5-methylchromone in a liquid carrier.

2. The composition of claim 1 further including between 15% and 85% of a liquid carrier.

3. The composition of claim 1 further including between 1% and 85% of a liquid carrier.

4. A purified and isolated compound having the formula:

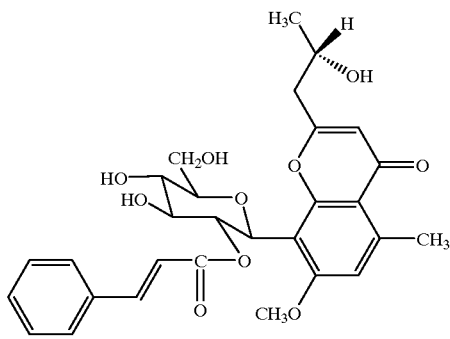

\* \* \* \* \*